(12) United States Patent
Verschuren et al.

(10) Patent No.: US 11,402,374 B2
(45) Date of Patent: Aug. 2, 2022

(54) METHOD OF DETECTING LABEL PARTICLES

(71) Applicant: Siemens Healthineers Nederland B.V., The Hague (NL)

(72) Inventors: Coen Adrianus Verschuren, Eindhoven (NL); Dominique Maria Bruls, Heeze (NL); Albert Hendrik Jan Immink, Eindhoven (NL); Femke Karina De Theije, Berghem (NL); Thea van der Wijk, Bunnik (NL); Alexander Marc Van Der Lee, Venlo (NL); Johannes Joseph Hubertina Barbara Schleipen, Eindhoven (NL)

(73) Assignee: Siemens Healthineers Nederland B.V., The Hague (NL)

( * ) Notice: Subject to any disclaimer, the term of this patent is extended or adjusted under 35 U.S.C. 154(b) by 209 days.

(21) Appl. No.: 14/707,124

(22) Filed: May 8, 2015

(65) Prior Publication Data
US 2015/0241416 A1   Aug. 27, 2015

Related U.S. Application Data

(62) Division of application No. 12/518,164, filed as application No. PCT/IB2007/054979 on Dec. 10, 2007, now Pat. No. 9,658,219.

(30) Foreign Application Priority Data

Dec. 12, 2006   (EP) .................................... 06125907

(51) Int. Cl.
*G01N 33/543*   (2006.01)
*G01N 21/552*   (2014.01)
(Continued)

(52) U.S. Cl.
CPC .............. *G01N 33/543* (2013.01); *B01L 3/50* (2013.01); *G01N 21/552* (2013.01);
(Continued)

(58) Field of Classification Search
None
See application file for complete search history.

(56) References Cited

U.S. PATENT DOCUMENTS 3,770,380 A   11/1973   Smith
3,939,350 A   2/1976   Kronick et al.
(Continued)

FOREIGN PATENT DOCUMENTS

CN   1424584 A   6/2003
EP   0254430 A2   1/1988
(Continued)

OTHER PUBLICATIONS

Sutherland et al., "Optical Detection of Antibody-Antigen Reactions at a Glass-Liquid Interface," Clinical Chemistry, vol. 30, No. 9, 1984, pp. 1533-1538.
(Continued)

*Primary Examiner* — Neil N Turk
(74) *Attorney, Agent, or Firm* — Dugan & Dugan, PC

(57) ABSTRACT

The invention relates to a method for the detection of target components that comprise label particles, for example magnetic particles (1). The method includes (a) collecting the target components at a binding surface (12, 112, 512) of a carrier (11, 111, 211, 311, 411, 511); (b) directing an input light beam (L1, L1a, L1b) into the carrier such that it is totally internally reflected in an investigation region (13, 313a, 313b) at the binding surface (12, 112, 512); and (c) determining the amount of light of an output light beam (L2, L2a, L2b) that comprises at least some of the totally internally reflected light. Evanescent light generated during
(Continued)

the total internal reflection is affected (absorbed, scattered) by target components and/or label particles (1) at the binding surface (12) and will therefore be missing in the output light beam (L2). This can be used to determine the amount of target components at the binding surface (12) from the amount of light in the output light beam (L2, L2*a*, L2*b*). A magnetic field generator (41) is optionally used to generate a magnetic field (B) at the binding surface (12) by which magnetic label particles (1) can be manipulated, for example attracted or repelled.

4 Claims, 8 Drawing Sheets

(51) Int. Cl.
  *G01N 21/64* (2006.01)
  *G01N 27/74* (2006.01)
  *B01L 3/00* (2006.01)
  *G01N 21/25* (2006.01)
  *G01N 21/45* (2006.01)

(52) U.S. Cl.
  CPC ......... *G01N 21/553* (2013.01); *G01N 21/648* (2013.01); *G01N 21/6428* (2013.01); *G01N 21/6452* (2013.01); *G01N 27/745* (2013.01); *G01N 33/54306* (2013.01); *G01N 33/54386* (2013.01); *B01L 2300/0636* (2013.01); *B01L 2300/0819* (2013.01); *G01N 21/253* (2013.01); *G01N 21/45* (2013.01); *Y10S 436/00* (2013.01)

(56) References Cited

U.S. PATENT DOCUMENTS

| | | |
|---|---|---|
| 3,975,084 A | 8/1976 | Block |
| 4,582,809 A * | 4/1986 | Block ............... G01N 21/6428 250/227.11 |
| 4,608,344 A | 8/1986 | Carter et al. |
| 4,857,273 A | 8/1989 | Stewart |
| 5,017,009 A | 5/1991 | Schutt et al. |
| 5,229,833 A | 7/1993 | Stewart |
| 5,341,215 A | 8/1994 | Seher |
| 5,350,697 A * | 9/1994 | Swope ................ G01N 21/47 356/246 |
| 5,429,951 A | 7/1995 | Bradwell |
| 5,437,840 A * | 8/1995 | King ................ G01N 21/552 356/136 |
| 5,512,492 A | 4/1996 | Herron et al. |
| 5,538,850 A | 7/1996 | King et al. |
| 5,866,434 A | 2/1999 | Massey |
| 5,922,537 A | 7/1999 | Ewart et al. |
| 6,362,011 B1 | 3/2002 | Massey et al. |
| 6,579,721 B1 | 6/2003 | Natan et al. |
| 6,891,868 B2 | 5/2005 | Verboom et al. |
| 7,081,192 B1 | 7/2006 | Wang et al. |
| 7,099,254 B2 | 8/2006 | Coops et al. |
| 7,361,479 B1 | 4/2008 | Haaheim |
| 7,498,145 B2 | 3/2009 | Uchiyama et al. |
| 7,502,303 B2 | 3/2009 | Kawamura |
| 7,619,960 B2 | 11/2009 | Kaisha |
| 7,948,858 B2 | 5/2011 | Kawamura et al. |
| 2004/0047770 A1 | 3/2004 | Schawaller et al. |
| 2004/0095871 A1 | 5/2004 | Shindo |
| 2005/0025676 A1 | 2/2005 | Ehrfeld et al. |
| 2005/0048599 A1 | 3/2005 | Goldbert et al. |
| 2005/0110989 A1 | 5/2005 | Schermer et al. |
| 2005/0117486 A1 | 6/2005 | Ishika |
| 2015/0241416 A1 | 8/2015 | Verschuren et al. |

FOREIGN PATENT DOCUMENTS

| | | |
|---|---|---|
| EP | 1079226 A1 | 2/2001 |
| EP | 1650547 A2 | 4/2006 |
| FR | 2050525 A5 | 4/1971 |
| GB | 2065298 A | 6/1981 |
| JP | 563273042 A | 11/1988 |
| JP | 2003296958 A | 10/2003 |
| JP | 2004039062 A | 2/2004 |
| JP | 2005077338 A | 3/2005 |
| JP | 2006196054 A | 7/2006 |
| RU | 2207564 C2 | 6/2003 |
| WO | 9522754 A1 | 8/1995 |
| WO | 9931486 A1 | 6/1999 |
| WO | 2000077525 A1 | 12/2000 |
| WO | 2005003787 A1 | 1/2005 |
| WO | 2005010542 A2 | 2/2005 |
| WO | 2005010543 A1 | 2/2005 |
| WO | 2007010469 A1 | 1/2007 |

OTHER PUBLICATIONS

Blickle et al. "Evanescent Light Scattering with Magnetic Colloids", Applied Physics Letters 87, pp. 101102-1-101102-3, 2005.
Wellman et al., "Magnetically-Assisted Transport Evanescent Field Fluoroimmunoassay", Analytical Chemistry, vol. 78, No. 13, Jul. 1, 2006, pp. 4450-4456.

* cited by examiner

METHOD OF DETECTING LABEL PARTICLES

CROSS REFERENCE TO RELATED APPLICATION

This application claims the benefit or priority of and describes the relationships between the following applications: wherein this application is a divisional of U.S. application Ser. No. 12/518,164, filed Jun. 8, 2009 and entitled "Microelectronic Sensor Device for Detecting Label Particles", which is the National Stage of International Application No. PCT/IB2007/054979 filed Dec. 10, 2007 and entitled "Microelectronic Sensor Device for Detecting Label Particles", all of which are incorporated herein in whole by reference.

The invention relates to a microelectronic sensor device and a method for the detection of target components, for example biological molecules, comprising label particles. Moreover, it relates to a carrier and a well-plate that are particularly suited for such a sensor device.

The US 2005/0048599 A1 discloses a method for the investigation of microorganisms that are tagged with particles such that a (e.g. magnetic) force can be exerted on them. In one embodiment of this method, a light beam is directed through a transparent material to a surface where it is totally internally reflected. Light of this beam that leaves the transparent material as an evanescent wave is scattered by microorganisms and/or other components at the surface and then detected by a photodetector or used to illuminate the microorganisms for visual observation.

Based on this situation it was an object of the present invention to provide means for an improved detection of target components comprising label particles. In particular, it is desired that the method is simple and that its sensitivity and/or accuracy is improved with respect to the state of the art.

This object is achieved by a method for detection of target components as described herein and defined in independent claim 1. Preferred embodiments are disclosed in the dependent claims.

The microelectronic sensor device according to the present invention serves for the qualitative or quantitative detection of target components comprising label particles, wherein the target components may for example be biological substances like biomolecules, complexes, cell fractions or cells. The term "label particle" shall denote a particle (atom, molecule, complex, nanoparticle, microparticle etc.) that has some property (e.g. optical density, magnetic susceptibility, electrical charge, fluorescence, radioactivity, etc.) which can be detected, thus indirectly revealing the presence of the associated target component. The microelectronic sensor device comprises the following components:

a) A carrier with a binding surface at which target components can collect. The term "binding surface" is chosen here primarily as a unique reference to a particular part of the surface of the carrier, and though the target components will in many applications actually bind to said surface, this does not necessarily need to be the case. All that is required is that the target components can reach the binding surface to collect there (typically in concentrations determined by parameters associated to the target components, to their interaction with the binding surface, to their mobility and the like). The carrier should have a high transparency for light of a given spectral range, particularly light emitted by the light source that will be defined below. The carrier may for example be produced from glass or some transparent plastic.

b) A light source for emitting a light beam, called "input light beam" in the following, into the aforementioned carrier such that it is totally internally reflected in an investigation region at the binding surface of the carrier. The light source may for example be a laser or a light emitting diode (LED), optionally provided with some optics for shaping and directing the input light beam. The "investigation region" may be a sub-region of the binding surface or comprise the complete binding surface; it will typically have the shape of a substantially circular spot that is illuminated by the input light beam. Moreover, it should be noted that the occurrence of total internal reflection requires that the refractive index of the carrier is larger than the refractive index of the material adjacent to the binding surface. This is for example the case if the carrier is made from glass (n=1.6) and the adjacent material is water (n=1.3). It should further be noted that the term "total internal reflection" shall include the case called "frustrated total internal reflection", where some of the incident light is lost (absorbed, scattered etc.) during the reflection process.

c) A light detector for determining the amount of light in an "output light beam", which comprises light that stems from the aforementioned total internal reflection of the input light beam. It is not necessary that the output light beam comprises all the totally internally reflected light (though this will preferably be the case), as some of this light may for example be used for other purposes or simply be lost, or that it completely consists of totally internally reflected light, as it may also comprise e.g. scattered light or fluorescence light.

The detector may comprise any suitable sensor or plurality of sensors by which light of a given spectrum can be detected, for example a photodiode, a photo resistor, a photocell, a CCD chip, or a photo multiplier tube.

The described microelectronic sensor device allows a sensitive and precise quantitative or qualitative detection of target components in an investigation region at the binding surface. This is due to the fact that the totally internally reflected input light beam generates an evanescent wave that extends from the carrier surface a short distance into the adjacent material. If light of this evanescent wave is scattered or absorbed by label particles bound to target components present at the binding surface, it will be missing in the output light beam. The amount of light in the output light beam (more precisely the amount of light missing in the output light beam when compared to the input light beam) is therefore an indication of the presence and the amount of label particles at the binding surface. One advantage of the described optical detection procedure comprises its accuracy as the evanescent waves explore only a small volume of typically 10 to 300 nm thickness directly above the binding surface, thus avoiding disturbances from the bulk material behind this volume. A high sensitivity is achieved when the reflected light is measured as all effects are detected that reduce the amount of totally internally reflected light. Moreover, the optical detection can optionally be performed from a distance, i.e. without mechanical contact between the carrier and the light source or light detector.

The microelectronic sensor device may particularly be designed such that the totally internally reflected light beam becomes frustrated resulting in a decrease of the totally internally reflected light intensity when the label-particles that are bound to the target components are macroscopic scattering and/or absorbing particles.

In a preferred embodiment of the invention, the microelectronic sensor device comprises a field generator for generating a magnetic and/or an electrical field that can affect the label particles. The field generator may for example be realized by a permanent magnet, a wire, a pair of electrodes, or a coil. The generated field may affect the label particles for instance by inducing a magnetization or a polarization and/or by exerting forces on them. Such a microelectronic sensor device allows a versatile manipulation of target components via fields, which may for example be used to accelerate the collection of target components at the binding surface and/or to remove undesired (unbound or, in a stringency test, weakly bound) components from the binding surface.

In the general case, the space next to the carrier at the side of the binding surface may be arbitrarily designed. It is for example possible that this space is exterior to the microelectronic sensor device and that target components are applied to the binding surface by spraying or painting; the space may also be open to the surroundings for detecting target components in e.g. the ambient atmosphere. Moreover, it is possible that the target components reach the binding surface through the carrier, e.g. by diffusion. In preferred embodiments of the invention, the microelectronic sensor device comprises however a sample chamber which is located adjacent to the binding surface and in which a sample with target components can be provided. The sample chamber is typically an empty cavity or a cavity filled with some substance like a gel that may absorb a sample substance; it may be an open cavity, a closed cavity, or a cavity connected to other cavities by fluid connection channels.

As was already mentioned, the microelectronic sensor device may be used for a qualitative detection of target components, yielding for example a simple binary response with respect to a particular target molecule ("present" or "not-present"). Preferably the sensor device comprises however an evaluation module for quantitatively determining the amount of target components in the investigation region from the detected output light beam. This can for example be based on the fact that the amount of light in an evanescent light wave, that is absorbed or scattered by label particles, is proportional to the concentration of the target components bound to the label particles in the investigation region. The amount of target components in the investigation region may in turn be indicative of the concentration of these components in an adjacent sample fluid according to the kinetics of the related binding processes.

In a further development of the aforementioned embodiment, the microelectronic sensor device comprises a recording module for monitoring the determined amount of light in the output light beam over an observation period. Thus it will be possible to monitor the kinetics with which target components collect at or depart from the binding surface. This may reveal valuable information about the target components and/or the prevailing ambient conditions. The evaluation module and/or the recording module are typically coupled to the light detector and may be realized by some data processing hardware, e.g. a microcomputer, together with associated software.

Up to now the description of the microelectronic sensor device included the case that only a single investigation region is present on the binding surface. In the following, several embodiments of the microelectronic sensor device will be considered in which the carrier comprises a plurality of investigation regions at which different input light beams can be totally internally reflected. One carrier then allows the processing of several investigation regions and thus for example the search for different target components, the observation of the same target components under different conditions and/or the sampling of several measurements for statistical purposes. The "different input light beams" may optionally be components of one broad light beam that is homogeneously generated by the light source.

The different input light beams that are used in the aforementioned embodiment may be different with respect to time. This is for example the case if the microelectronic sensor device comprises a scanning module for sequentially coupling the light source to different investigation regions. Alternatively or additionally, it may comprise a scanning module for optically coupling the light detector to different investigation regions on the binding surface. The scanning modules may for example comprise optical components like lenses or mirrors for directing the incident or the output light beam in a suitable way. The scanning modules may also comprise means for moving the carrier with respect to the light source and/or light detector.

In another embodiment of the microelectronic sensor device with a plurality of investigation regions, a plurality of light sources and/or a plurality of light detectors is present that are directed to different investigation regions at the binding surface. In this case it is possible to process a plurality of investigation regions simultaneously, thus speeding-up the associated measurement process accordingly. This embodiment can of course be combined with the previous one, i.e. there may for example be a scanning module for scanning the input light beams of a plurality of light sources over different arrays of investigation regions and/or a scanning module for directing the output light beams from different arrays of investigation regions to a plurality of light detectors. By using scanning modules, the number of light sources/detectors can be kept smaller than the number of investigation regions.

In another embodiment with a plurality of investigation regions, the microelectronic sensor device comprises a plurality of individually controllable (magnetic or electrical) field generators that are associated to different investigation regions. In this case it is possible to manipulate the label particles in each investigation region individually according to the requirements of the particular tests that shall be performed there.

The microelectronic sensor device may in principle be used with any kind of label particles. It is however preferably provided with label particles that specifically fit to the other components of the device. The sensor device may especially comprise label particles with a mantle of a transparent material, wherein this mantle typically covers (completely or partially) one or more kernels of another material, e.g. iron-oxide grains. In this case light of an evanescent light wave at the binding surface can readily enter the label particles where it is absorbed and/or scattered and thus lost for the output light beam. The transparent material of the mantle may particularly be a material with a similar refractive index as the material of the carrier, because this optimizes the transition of light from the carrier to the label particles. The mantle may for example consist of the same material as the carrier.

The microelectronic sensor device may optionally comprise a "second light detector" for determining (qualitatively or quantitatively) fluorescence light emitted by target components at the binding surface. The fluorescence can be stimulated by the evanescent wave of the input light beam in a small volume adjacent to the binding surface and then be detected, thus indicating the presence (and amount) of fluorescent target components.

In another embodiment of the invention, the microelectronic sensor device comprises an input-light monitoring sensor for determining the amount of light in the input light beam. This allows to take said amount into consideration during a (quantitative) evaluation of the measurements of the output light beam and/or to control the input light beam in a feedback loop.

The input-light monitoring sensor can be integrated into the light source, which provides a robust and compact design and which is favorable for an integration in a feedback control loop. Alternatively, the input-light monitoring sensor (or at least a part of it) can be disposed outside the light source as an independent component. The latter arrangement has the advantage that the measurement of this sensor can be better focused on the actual input light beam as it enters the carrier because the monitoring measurement takes place behind optical elements like lenses or pinholes that are typically present in the light path of the light source.

It was already mentioned that the measurement results of the input-light monitoring sensor can be related to the amount of light in the output light beam that is determined by the light detector. The microelectronic sensor device may therefore comprise an evaluation module that is adapted to execute such a relation. To this end, the evaluation module is typically provided with signals from the input-light monitoring sensor and the light detector which represent the determined amounts of light. The evaluation module may optionally preprocess these signals, e.g. (low-pass) filter them. In a preferred embodiment, the amount of light in the output light beam is normalized by the amount of light in the input light beam, making the result independent of variations in the power of the light source.

According to another embodiment of the invention, the light source is adapted to generate a polarized input light beam, particularly a linearly polarized input light beam. In a polarized light beam, the vectors of the electrical field (and thus also of the associated magnetic field) are not randomly oriented in the plane perpendicular to the direction of propagation of the light beam but have a regular orientation. This orientation is constant in space for a linearly polarized light beam and rotates in a regular manner for a circularly or elliptically polarized light beam. Generating an input light beam with a polarization provides it with a characteristic internal feature that affects the interaction of this beam with other entities, e.g. with optical components in the light path or with target particles to be detected. This opens many possibilities that can favorably be exploited, for example the possibility to distinguish light in the output light beam that stems from the input light beam from light of other sources, e.g. the ambience.

In a preferred realization of the aforementioned embodiment, the input light beam has a linear polarization in the plane of incidence with respect to an entrance window of the carrier at which the input light beam enters the carrier. Additionally or alternatively, the output light beam may have a linear polarization in the plane of incidence with respect to an exit window of the carrier at which the output light beam leaves the carrier. As usual, the "plane of incidence" of a light beam refers to the plane that comprises said light beam and that is perpendicular to the surface on which said light beam impinges. When a light beam impinges on a surface of the carrier, a (small) fraction of its light will usually be reflected. Besides the fact that this light is lost for other purposes, a particular disadvantage of such a reflection is that it may disturb other components, e.g. the light detector or a laser in the light source. It is therefore desirable to reduce the amount of light that is reflected at the entrance or exit window of the carrier. Such a reduction is possible with the proposed setup in which the input light beam and/or the output light beam have the explained polarization.

In a preferred embodiment of the invention, the entrance window through which the input light beam enters the carrier is placed under Brewster angle with respect to the input light beam and/or the exit window through which the output light beam leaves the carrier is placed under Brewster angle with respect to the output light beam. As is well known from optics, a reflected beam vanishes if an incident light beam with a linear polarization in the plane of incidence impinges on a surface under the corresponding Brewster angle. If this embodiment is combined with the aforementioned one (having a linearly polarized input light beam), the reflections at the entrance or exit window of the carrier can be completely suppressed. The Brewster angle for a particular setup can be calculated from the fact that, at Brewster angle of incidence, there is an angle of 90° between the refracted light beam and the direction of the (suppressed) reflected light beam.

The invention further relates to a carrier for providing a sample to be investigated, wherein said carrier may particularly be suited as a carrier for a microelectronic sensor device of the kind described above. The carrier comprises a sample chamber in which a sample can be provided and which has a transparent inspection wall. The inspection wall has on its interior side a binding surface at which components of a sample can collect. On its exterior side, the inspection wall has at least one optical structure which is designed such that (i) an input light beam which is directed from outside the carrier onto the optical structure enters the inspection wall, (ii) said input light beam is (at least one times) totally internally reflected in an investigation region at the binding surface, and (iii) an output light beam comprising at least some of the totally internally reflected light and/or fluorescence light emitted by target components at the binding surface leaves the inspection wall through the optical structure, preferably in a direction away from the carrier.

The inspection wall will typically have the basic form of a plate with a substantially parallel interior and exterior surface, wherein the interior surface comprises the binding surface and wherein the optical structure projects outwards from the exterior surface. Moreover, the inspection wall can in principle be any part of the wall of the sample chamber, for example a side wall or the top. Preferably, the inspection wall is however a part of the bottom of the carrier (or the whole bottom), which has two advantages: First, sample components underlying sedimentation will concentrate at the binding surface of the bottom. Second, the components of an associated instrument can be disposed below said bottom, thus leaving space at the sides of the carrier for a possible arrangement of further carriers.

The described carrier has the advantage that a sample inside its sample chamber can optically be investigated with an input light beam that is totally internally reflected, thus providing an evanescent field in a small volume at the binding surface. Effects like absorption or scattering taking place in this small volume will affect the output light beam which leaves the carrier. Additionally, fluorescence may be stimulated by the evanescent wave in fluorescent target components and thus provide a further indicator for the target. As both the input light beam and the output light beam are directed from the outside towards the carrier or vice versa, the corresponding light source and light detector can be arranged a distance away and separate from the carrier.

The invention further relates to a well-plate which comprises a plurality of carriers of the kind described above, i.e. a plurality of sample chambers with transparent inspection walls having on their interior side a binding surface and on their exterior side at least one optical structure, wherein said optical structure allows an input light beam coming from outside the carrier to enter the inspection wall, to be totally internally reflected at the binding surface, and then to leave the inspection wall as an output light beam that is directed away from the carrier.

The well-plate combines a plurality of the carriers described above in an array and thus allows a parallel investigation of a multitude of samples and/or of one sample in a multitude of investigation assays. As the well-plate is based on the described carrier, reference is made to the above description for more details on the advantages, features and improvements of said well-plate.

In the following various embodiments of the invention will be described that can be applied to a microelectronic sensor device, a carrier and a well-plate of the kind described above.

While it is in principle possible that the carrier has some dedicated structure with multiple components of different materials, it is preferred that the carrier is homogenously fabricated from a transparent material, for example a transparent plastic. The carrier can thus readily be produced for example by injection moulding.

The investigation region of the carrier has preferably a low roughness in order to minimize unwanted influences on the (frustrated) total internal reflection. With $\lambda$ being a characteristic (e.g. peak or average) wavelength of the light constituting the input light beam, the roughness of the investigation region is preferably less than $0.5\lambda$, most preferably less than $0.1\lambda$ (which means that the height difference between microscopic "valleys" and "tips" of the carrier surface in the investigation region is smaller than these values).

The investigation region of the carrier may optionally be covered with at least one type of capture element that can bind one or more target components. A typical example of such a capture element is an antibody to which corresponding antigens can specifically bind. By providing the investigation region with capture elements that are specific to certain target components, it is possible to selectively enrich these target components in the investigation region. Moreover, undesired target components can be removed from the binding surface by suitable (e.g. magnetic) repelling forces (that do not break the bindings between desired target components and capture elements). The binding surface may preferably be provided with several types of capture elements that are specific for different target components. In a microelectronic sensor device with a plurality of investigation regions, there are preferably at least two investigation regions having different capture elements such that these regions are specific for different target components.

According to another embodiment of the invention, the surface of the carrier is substantially perpendicular to the input light beam and/or to the output light beam at the entrance window or exit window where this beam enters or leaves the carrier, respectively, i.e. the angle of incidence lies in a range of about ±5° around 90°. In this case the direction of the input light beam and/or the output light beam will not or only minimally change during the transition from a surrounding medium into the carrier or vice versa. Moreover, reflection will be minimized. Additionally or alternatively, the corresponding regions may also have an anti-reflection coating. To prevent optical feedback into the light source (e.g. a laser), it may be preferable to have the incident beam (at most) a few degrees off-perpendicular.

The carrier may particularly comprise at least one surface with a form similar or identical to a hemisphere or a truncated pyramid. As will be discussed in more detail with reference to the Figures, these forms function like lenses and/or prisms and thus provide a favorable guidance of the incident and the output light beam.

The carrier may further optionally comprise a cavity in which a (magnetic or electrical) field generator can at least partially be disposed. The source of the field can thus be positioned as close as possible to the binding surface, allowing to generate high field strengths in the investigation region with minimal effort (e.g. electrical currents) and with minimal disturbances for other regions (e.g. neighboring investigation regions). Moreover, such a cavity can be used to center the carrier with respect to the field generator, the light source and the light detector.

While the microelectronic sensor device may in principle be constructed as a "one-piece" unit of solidly mounted components, it is preferred that the carrier is designed as an exchangeable component of the device, for example a well-plate. Thus it may be used as a low-cost disposable part, which is particularly useful if it comes into contact with biological samples and/or if its coating (e.g. with antibodies) is used up during one measurement process.

The invention further relates to a method for the detection of target components comprising label particles, wherein said method comprises the following steps:
 a) Collecting target components at the binding surface of a carrier.
 b) Directing an input light beam into the carrier such that it is totally internally reflected in an investigation region at the binding surface.
 c) Determining the amount of light in an output light beam which comprises at least some of the totally internally reflected light of the input light beam; preferably the output light beam comprises only such totally internally reflected light.

The method comprises in general form the steps that can be executed with a microelectronic sensor device of the kind described above. Therefore, reference is made to the preceding description for more information on the details, advantages and improvements of that method.

In an embodiment of the method, the label particles are manipulated by a magnetic and/or an electrical field, wherein this manipulation may particularly comprise the attraction of the particles to or their repulsion from the investigation region.

In another embodiment of the method, the amount of light in the input light beam is measured and related to the measured amount of light in the output light beam. Thus variations in the intensity of the input light beam can be detected and used to e.g. correct the measured amount of light in the output light beam, making the result independent of input light fluctuations.

These and other aspects of the invention will be apparent from and elucidated with reference to the embodiment(s) described hereinafter. These embodiments will be described by way of example with the help of the accompanying drawings in which:

FIG. 1 schematically shows the general setup of a microelectronic sensor device according to the present invention;

Like reference numbers or numbers differing by integer multiples of 100 refer in the Figures to identical or similar components.

Figure 1:
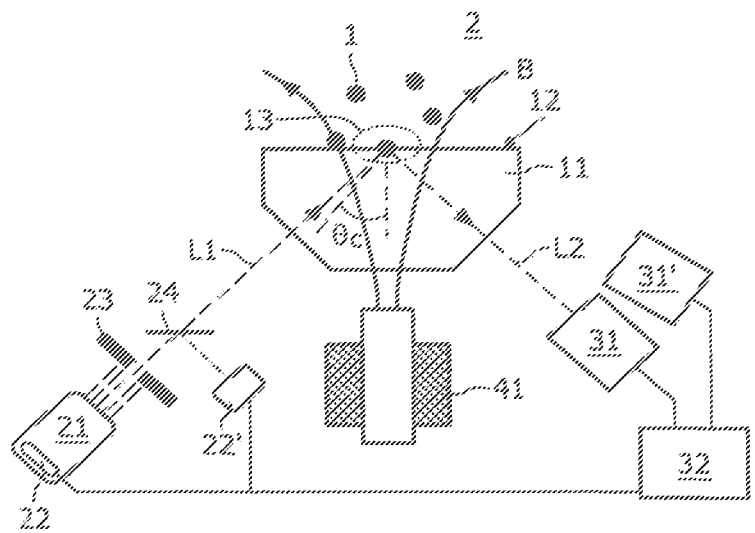

FIG. 1 shows the general setup of a microelectronic sensor device according to the present invention. A central component of this device is the carrier 11 that may for example be made from glass or transparent plastic like poly-styrene. The carrier 11 is located next to a sample chamber 2 in which a sample fluid with target components to be detected (e.g. drugs, antibodies, DNA, etc.) can be provided. The sample further comprises magnetic particles 1, for example superparamagnetic beads, wherein these particles 1 are usually bound as labels to the aforementioned target components (for simplicity only the magnetic particles 1 are shown in the Figure).

The interface between the carrier 11 and the sample chamber 2 is formed by a surface called "binding surface" 12. This binding surface 12 may optionally be coated with capture elements, e.g. antibodies, which can specifically bind the target components.

The sensor device comprises a magnetic field generator 41, for example an electromagnet with a coil and a core, for controllably generating a magnetic field B at the binding surface 12 and in the adjacent space of the sample chamber 2. With the help of this magnetic field B, the magnetic particles 1 can be manipulated, i.e. be magnetized and particularly be moved (if magnetic fields with gradients are used). Thus it is for example possible to attract magnetic particles 1 to the binding surface 12 in order to accelerate the binding of the associated target component to said surface.

The sensor device further comprises a light source 21, for example a laser or an LED, that generates an input light beam L1 which is transmitted into the carrier 11. The input light beam L1 arrives at the binding surface 12 at an angle larger than the critical angle $\theta_c$ of total internal reflection (TIR) and is therefore totally internally reflected as an "output light beam" L2. The output light beam L2 leaves the carrier 11 through another surface and is detected by a light detector 31, e.g. a photodiode. The light detector 31 determines the amount of light of the output light beam L2 (e.g. expressed by the light intensity of this light beam in the whole spectrum or a certain part of the spectrum). The measurement results are evaluated and optionally monitored over an observation period by an evaluation and recording module 32 that is coupled to the detector 31.

In the light source 21, a commercial DVD ($\lambda$=658 nm) laser-diode can be used. A collimator lens may be used to make the input light beam L1 parallel, and a pinhole 23 of e.g. 0.5 mm may be used to reduce the beam diameter. For accurate measurements, a highly stable light source is required. However, even with a perfectly stable power source, temperature changes in the laser can cause drifting and random changes in the output.

To address this issue, the light source may optionally have an integrated input light monitoring diode 22 for measuring the output level of the laser. The (low-pass filtered) output of the monitoring sensor 22 can then be coupled to the evaluation module 32, which can divide the (low-pass filtered) optical signal from the detector 31 by the output of the monitoring sensor 22. For an improved signal-to-noise ratio, the resulting signal may be time-averaged. The division eliminates the effect of laser output fluctuations due to power variations (no stabilized power source needed) as well as temperature drift (no precautions like Peltier elements needed).

A further improvement can be achieved if not (or not only) the laser output itself is measured, but the final output of the light source 21. As FIG. 1 coarsely illustrates, only a fraction of the laser output exits the pinhole 23. Only this fraction will be used for the actual measurement in the carrier 11, and is therefore the most direct source signal. Obviously, this fraction is related to the output of the laser, as determined by e.g. the integrated monitor diode 22, but will be affected by any mechanical change or instability in the light path (a laser beam profile is approximately elliptical with a Gaussian profile, i.e. quite non-uniform). Thus, it is advantageous to measure the amount of light of the input light beam L1 after the pinhole 23 and/or after eventual other optical components of the light source 21. This can be done in a number of ways, for example:

a parallel glass plate 24 can be placed under 45° or a beam splitter cube (e.g. 90% transmission, 10% reflection) can be inserted into the light path behind the pinhole 23 to deflect a small fraction of the light beam towards a separate input-light monitoring sensor 22';

a small mirror at the edge of the pinhole 23 or the input light beam L1 can be used to deflect a small part of the beam towards a detector.

The Figure shows a "second light detector" 31' that can alternatively or additionally be used to detect fluorescence light emitted by fluorescent particles 1 which were stimulated by the evanescent wave of the input light beam L1. As this fluorescence light is usually emitted isotropically to all sides, the second detector 31' can in principle be disposed anywhere, e.g. also above the binding surface 12. Moreover, it is of course possible to use the detector 31, too, for the sampling of fluorescence light, wherein the latter may for example spectrally be discriminated from reflected light L2.

The described microelectronic sensor device applies optical means for the detection of magnetic particles 1 and the target components for which detection is actually of interest. For eliminating or at least minimizing the influence of background (e.g. of the sample fluid, such as saliva, blood, etc.), the detection technique should be surface-specific. This is achieved by using the principle of frustrated total internal reflection which is explained in the following.

According to Snell's law of refraction, the angles $\theta_A$ and $\theta_B$ with respect to the normal of an interface between two media A and B satisfy the equation $$n_A \sin \theta_A = n_B \sin \theta_B$$

with $n_A$, $n_B$ being the refractive indices in medium A and B, respectively. A ray of light in a medium A with high refractive index (e.g. glass with $n_A=2$) will for example refract away from the normal under an angle $\theta_B$ at the interface with a medium B with lower refractive index such as air ($n_B=1$) or water ($n_B\approx1.3$). A part of the incident light will be reflected at the interface, with the same angle as the angle $\theta_A$ of incidence. When the angle $\theta_A$ of incidence is gradually increased, the angle $\theta_B$ of refraction will increase until it reaches 90°. The corresponding angle of incidence is called the critical angle, $\theta_c$, and is given by $\sin \theta_c = n_B/n_A$. At larger angles of incidence, all light will be reflected inside medium A (glass), hence the name "total internal reflection". However, very close to the interface between medium A (glass) and medium B (air or water), an evanescent wave is formed in medium B, which decays exponentially away from the surface. The field amplitude as function of the distance z from the surface can be expressed as:

$$\exp\left(-k\sqrt{n_A^2\sin^2(\theta_A)-n_B^2}\cdot z\right)$$

with $k=2\pi/\lambda$, $\theta_A$ being the incident angle of the totally reflected beam, and $n_A$ and $n_B$ the refractive indices of the respective associated media.

For a typical value of the wavelength $\lambda$, e.g. $\lambda=650$ nm, and $n_A=1.53$ and $n_B=1.33$, the field amplitude has declined to $\exp(-1)\approx 0.37$ of its original value after a distance z of about 228 nm. When this evanescent wave interacts with another medium like the magnetic particles 1 in the setup of FIG. 1, part of the incident light will be coupled into the sample fluid (this is called "frustrated total internal reflection"), and the reflected intensity will be reduced (while the reflected intensity will be 100% for a clean interface and no interaction). Depending on the amount of disturbance, i.e. the amount of magnetic beads on or very near (within about 200 nm) to the binding surface 12 (not in the rest of the sample chamber 2), the reflected intensity will drop accordingly. This intensity drop is a direct measure for the amount of bonded magnetic beads 1, and therefore for the concentration of target molecules. When the mentioned interaction distance of the evanescent wave of about 200 nm is compared with the typical dimensions of anti-bodies, target molecules and magnetic beads, it is clear that the influence of the background will be minimal. Larger wavelengths $\lambda$ will increase the interaction distance, but the influence of the background liquid will still be very small.

The described procedure is independent of applied magnetic fields. This allows real-time optical monitoring of preparation, measurement and washing steps. The monitored signals can also be used to control the measurement or the individual process steps.

For the materials of a typical application, medium A of the carrier 11 can be glass and/or some transparent plastic with a typical refractive index of 1.52. Medium B in the sample chamber 2 will be water-based and have a refractive index close to 1.3. This corresponds to a critical angle $\theta_c$ of 60°. An angle of incidence of 70° is therefore a practical choice to allow fluid media with a somewhat larger refractive index (assuming $n_A=1.52$, $n_B$ is allowed up to a maximum of 1.43). Higher values of $n_B$ would require a larger $n_A$ and/or larger angles of incidence.

Advantages of the described optical read-out combined with magnetic labels for actuation are the following:

Cheap cartridge: The carrier cartridge 11 can consist of a relatively simple, injection-molded piece of polymer material that may also contain fluidic channels.

Large multiplexing possibilities for multi-analyte testing: The binding surface 12 in a disposable cartridge can be optically scanned over a large area. Alternatively, large-area imaging is possible allowing a large detection array. Such an array (located on an optical transparent surface) can be made by e.g. ink-jet printing of different binding molecules on the optical surface. The method also enables high-throughput testing in well-plates by using multiple beams and multiple detectors and multiple actuation magnets (either mechanically moved or electro-magnetically actuated).

Actuation and sensing are orthogonal: Magnetic actuation of the magnetic particles (by large magnetic fields and magnetic field gradients) does not influence the sensing process. The optical method therefore allows a continuous monitoring of the signal during actuation. This provides a lot of insights into the assay process and it allows easy kinetic detection methods based on signal slopes.

The system is really surface sensitive due to the exponentially decreasing evanescent field.

Easy interface: No electrical interconnect between cartridge and reader is necessary. An optical window is the only requirement to probe the cartridge. A contact-less read-out can therefore be performed.

Low-noise read-out is possible.

Figure 2:
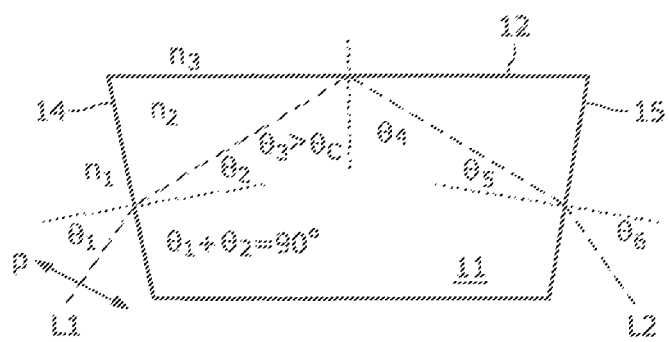
FIG. 2 shows the angles of incidence when the input light beam and the output light beam are oriented under Brewster angle.

FIG. 2 illustrates in more detail the angles of incidence of the input light beam L1 and the output light beam L2 at the entrance window 14, the binding surface 12, and the exit window 15 of a carrier 11. When the entrance and exit windows 14, 15 are orthogonal to the incoming beam, normally a part of the light (typically around 4%) is reflected back, causing e.g. in the light source 21 non-desirable output fluctuations of a laser (called "laser feedback"). This distorts the measurement. Furthermore, interference effects can occur in the light detector at the detection side as well, as typically a perpendicular orientation is used here, too, and a coherent light source (laser) is used.

Due to unwanted heating of the measurement cartridge, which occurs e.g. due to the heating of the actuation magnets 41 during operation or due to other external factors, a slight shift of the positions of the carrier's facets can lead to slow variations of the intensity, on both the light source and the detection branch of the setup, that are difficult to eliminate from the measurement. By placing the light detector at an angle (rather than perpendicular) with respect to the incoming output light beam L2, some of the problems occurring at the detection side of the setup can already be eliminated effectively. At the light source side, however, this is not possible.

It is therefore desirable to make the entrance and exit windows 14, 15 of the carrier 11 such that reflections are eliminated without the use of expensive optical anti-reflex coatings.

To solve this problem, it is proposed to place the entrance and exit windows 14, 15 under Brewster angle with respect to the incoming light beam, and to provide this beam with a (linear) polarization in the plane of incidence (called "p-polarization"). As is known from optics (cf. e.g. Pedrotti & Pedrotti, Introduction to Optics, Prentice Hall), a reflected beam vanishes if the p-polarized incident beam hits the surface of a (transparent) medium under Brewster angle.

A p-polarized input light beam L1 can be achieved by choosing the right orientation of a semiconductor laser in the light source, or by using a half wave plate to rotate the polarization to the correct orientation.

The propagation of the input light beam L1 inside the carrier 11 is fixed due to the fact that it should impinge on the binding surface 12 with an angle $\theta_3$ larger than the critical angle $\theta_c$ of TIR. This fixes also the orientation of the entrance and exit windows or facets of the carrier 11, if their angle $\theta_2$ or $\theta_6$, respectively, with the refracted beam shall correspond to the Brewster angle. This in turn fixes the direction of the input light beam L1 and the output light beam L2.

The angle of incidence $\theta_1$ of the input light beam L1 is equal to Brewster angle when the sum of this angle and the angle $\theta_2$ of refraction is 90°. This condition in combination with Snell's law leads to the following formula for the angle of incidence at Brewster angle:

$$\tan(\theta_1) = n_2/n_1,$$

where $n_1$ is the refractive index of the medium in which the input light beam L1 propagates before refraction, normally air, and $n_2$ of the medium where the refracted ray propagates, normally the plastic of the carrier (e.g. polycarbonate, zeonex or polystyrene).

For the angle $\theta_2$ of the refracted beam one finds $$\tan(\theta_2) = n_1/n_2.$$

Another condition that needs to be satisfied is that the input light beam L1 should be incident at an angle $\theta_3$ close to but beyond the critical angle $\theta_c$ of total internal reflection at the binding surface 12, i.e.

$$\theta_3 > \theta_c \text{ with } \sin(\theta_c) = n_3/n_2,$$

where $n_3$ is the refractive index of the medium above the binding surface 12. Furthermore, the angles at the side of the output light beam L2 are mirrored with respect to the input side, i.e.

$$\theta_4 = \theta_3, \theta_5 = \theta_2, \text{ and } \theta_6 = \theta_1.$$

For typical values of $n_1 = 1$ (air), $n_2 = 1.5$ (transparent plastic), and $n_3 = 1.3$ (water like), the following figures can be derived: $\theta_3 = \theta_4 > 60°$, $\theta_1 = \theta_6 = 56°$, $\theta_2 = \theta_5 = 34°$.

By placing the entrance and exit windows of the carrier at Brewster angle, unwanted reflections back into the laser are prevented without the need of an expensive anti-reflection coating. Furthermore, by placing the detector at an angle, rather than perpendicular, interference effects on the detector side can be prevented as well. By doing so, expansion or shrinkage of the carrier/cartridge during a measurement, e.g. due to thermal effects, will not influence the measurement result.

In the environment of a laboratory, well-plates are typically used that comprise an array of many sample chambers ("wells") in which different tests can take place in parallel. FIGS. 3-7 show different possible embodiments of one well of such a well-plate that are particularly suited for an application of the explained measurement principle. The production of these (disposable) wells is very simple and cheap as a single injection-moulding step is sufficient.

Figure 3:
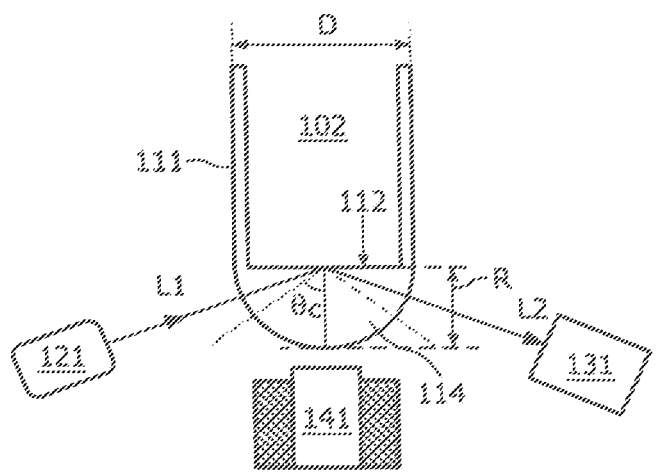
FIG. 3 shows a microelectronic sensor device with a well having a spherical bottom.

The light source 121 shown in FIG. 3 is arranged to produce a parallel light beam L1, incident at the well bottom surface at an angle larger than the critical angle $\theta_c$. To prevent excess reflection of this input light beam L1 at the first interface from air to the carrier 111 (e.g. glass or plastic material), the bottom of the well comprises a hemispherical shape 114 of radius R, with its centre coinciding with the detection surface 112. The input light beam L1 is directed towards this same centre. At the reflection side, a photodetector such as a photodiode 131 is positioned to detect the intensity of the output light beam L2. A typical diameter D of the well 102 ranges from 1 to 8 mm. The Figure further indicates a magnet 141 for generating magnetic actuation fields inside the well 102 (this magnet is not shown in the following Figures for simplicity).

Figure 4:
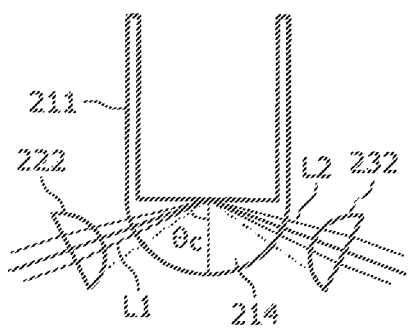
FIG. 4 shows the design of FIG. 3 with additional means for focusing a light beam.

FIG. 4 shows an alternative embodiment in which the light source comprises some optical element like a lens 222 to produce an input light beam L1 which is substantially focused to the centre of the hemisphere 214. At the detection side, a similar optical element 232 can be used to collect and detect the light intensity of the output light beam L2.

Figure 5:
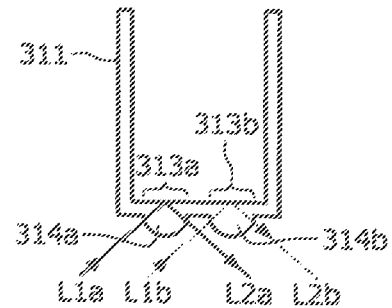
FIG. 5 shows a well having a plurality of hemispheres at the bottom.

In a further development of the measuring procedure, multiple input light beams and output light beams can be used to simultaneously detect the presence of different target molecules at different locations in the same well. FIG. 5 shows in this respect a well with multiple hemispheres 314a, 314b on the well bottom that can be used to couple the light from multiple input light beams L1a, L1b to respective investigation regions 313a, 313b on the bottom of the well. Multiple photodetectors (not shown) may be used in this case to measure the multiple output light beams L2a, L2b.

Figure 6:
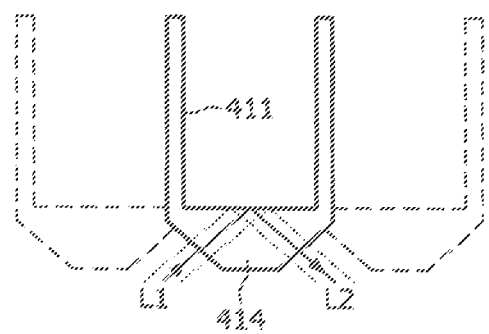
FIG. 6 shows a well having a bottom in the form of a truncated pyramid.

FIG. 6 shows an alternative embodiment in which a prism or truncated pyramidal structure 414 is used to couple the light of the input light beam L1 and the output light beam L2. The sloped edges of the pyramid should be substantially perpendicular to these light rays. Advantages of this design are that it is simple to produce and does not block beams from neighboring areas. Neighboring wells are indicated in this Figure by dashed lines.

As indicated in FIG. 6, it is possible to use a single, parallel input light beam L1 with a diameter covering all detection areas on the well bottom. As a detector, multiple photodiodes can be used, aligned with each individual detection area. Alternatively, a CCD or CMOS chip (not shown) such as used in a digital camera can be used to image the reflected intensity response of the entire well bottom, including all detection areas. Using appropriate signal processing, all signals can be derived as with the separate detectors, but without the need for prior alignment.

Figure 7:
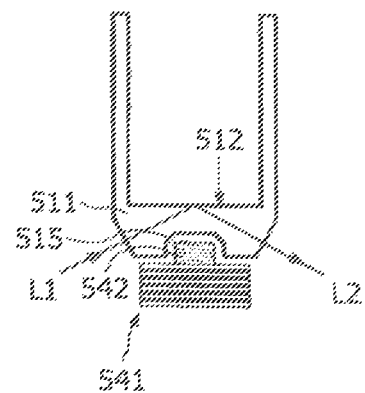
FIG. 7 shows the design of FIG. 6 with a cavity for an electromagnet.

FIG. 7 shows a further embodiment in which the well bottom 511 comprises an open cavity 515 with its center outside the optical path of the input light beam(s) L1 and the output light beam(s) L2. This allows the following advantageous features:

- A (T-shaped) ferrite core 542 of a magnetic coil 541 for improved field intensity and concentration can be placed close to the binding surface 512, allowing a compact and low-power design.
- A self-aligning structure is achieved: if the optics and the magnetic field generator 541 are fixed, an auto-alignment of the well on the ferrite core 542 takes place.

The magnetic beads 1 that are used in the described embodiments of the invention are typically poly-styrene spheres filled with small magnetic grains (e.g. of iron-oxide). This causes the beads to be super-paramagnetic. The refractive index of poly-styrene is nicely matched to the refractive index of a typical substrate material of well-plates. In this way optical outcoupling of light is enhanced.

Experimental Results A

In the following, some experimental results will be described that were obtained in a setup with a well-plate like that of FIG. 3. Standard 96 wells polystyrene titerplates were used with a flat bottom (6 mm in diameter, about 1 mm bottom thickness). To get the hemispherical bottom, glass lenses were attached to the bottom using refractive index matched immersion oil (n=1.55). The glass lenses were polished down from a hemispherical shape (6 mm diameter) to a thickness of 2 mm. The model assay chosen for the set of experiments is drugs of abuse in saliva. Drugs of abuse are generally small molecules that only possess one epitope and for this reason cannot be detected by a sandwich assay. A competitive or inhibition assay is the method to detect these molecules. A well-known competitive assay setup is to couple the target molecules of interest onto a surface, and link antibodies to a detection tag (e.g. enzyme, fluorophore, or magnetic particle). This system was used to perform a competitive assay between the target molecules from the sample and the target molecules on the surface, using the tagged antibodies. The tag in these experiments was a magnetic particle. Upon actuation, a permanent magnet was placed under the well by mechanical movement. The distance between the bottom of the well and the magnet was about 2 mm. A permanent magnet in the well was used for magnetic washing.

Figure 8:
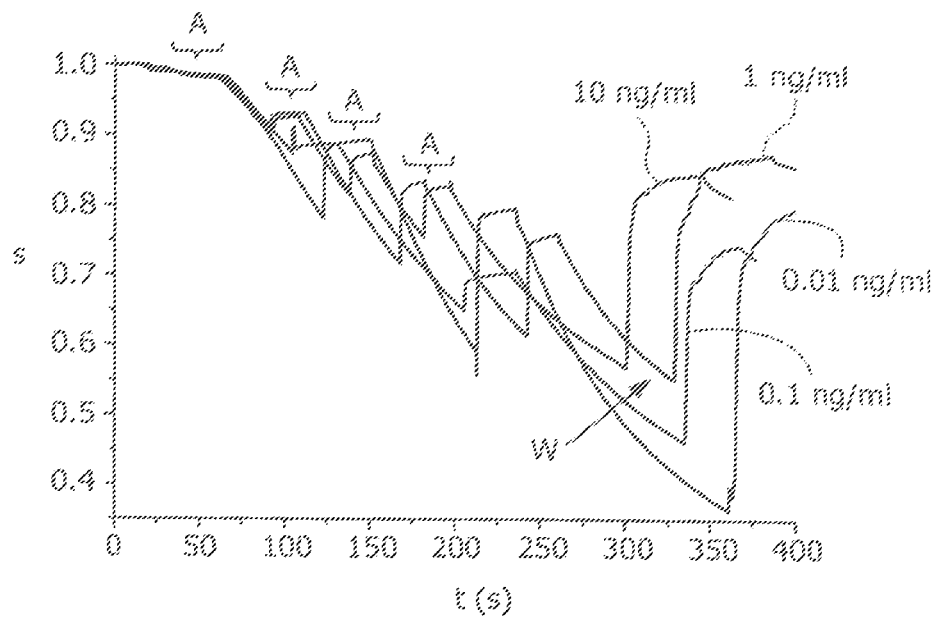
FIG. 8 is a diagram showing a normalized measurement signal s over time t for solutions with different concentrations of morphine labeled with magnetic particles.

FIG. 8 shows the normalized measurement signal s over time t for a first sensitivity test. For that, the bottom of a well was prepared for detection of the target molecules. The target under investigation was morphine. Morphine is a small molecule, with only one epitope, so a competitive assay has to be performed to indicate the amount of morphine in a sample. A clear polystyrene surface (96 wells titerplate) was coated for 2 hrs with a range of concentrations of BSA-morphine from 1 pg/ml to 1 µg/ml. Then functionalized superparamagnetic nanoparticles "MP" (300 nm Carboxyl-Adembeads functionalized with monoclonal anti morphine antibodies) solved in PBS+10 mg/ml BSA+ 0.65% Tween-20 were inserted into the wells (1:20 dilution of MPs, total amount of solution was 50 µl). The MPs were attracted to the surface by alternated application of magnetic forces (in the order of 10 fN) as indicated by symbol A in FIG. 8. In the end, unbound particles were removed from the surface by a washing step, indicated by symbol W in FIG. 8. The Figure shows that the lowest concentration of BSA-morphine (10 pg/ml) yields the largest dynamic measurement range. Also, the steepness of the curve after actuation is the largest, enabling fast response/short measuring time and the highest sensitivity.

Figure 9:
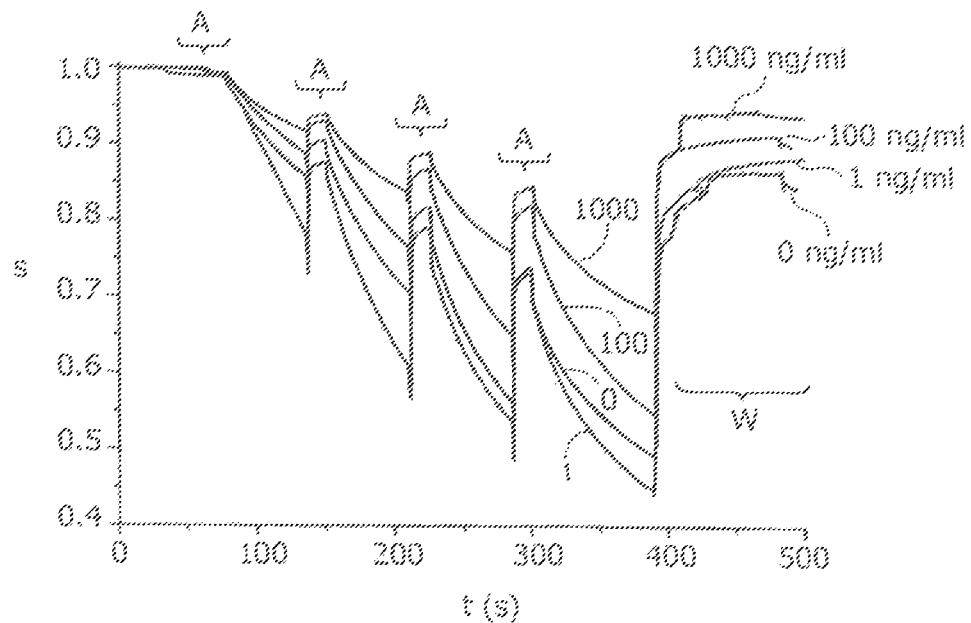
FIG. 9 is a diagram showing a normalized measurement signal s over time t for solutions containing morphine labeled with magnetic particles and different concentrations of free morphine.

To test the sensitivity of the assay, the ability of free morphine to compete for functionalized MP binding to the surface was tested. FIG. 9 shows the resulting normalized signal s collected by the detector as a function of time t. A clear polystyrene surface (96 wells titerplate) was coated for 2 hrs with 10 pg/ml BSA-morphine. MPs functionalized with anti-morphine antibodies premixed with a defined amount of free morphine solved in PBS+10 mg/ml BSA+ 0.65% Tween-20 were inserted into the wells (1:20 dilution of MPs, total amount of solution was 40 µl). As described above and indicated in the Figure, the MPs were actuated four times at t=30 s, t=140 s, t=210 s, t=290 s during 15 sec (cf. symbol A). At t=390 s the non-bound MPs have been removed from the well by means of magnetic washing W, i.e. the non-bound MPs are removed by applying a magnetic force using a permanent magnet in the fluid above the binding surface.

It can be seen from the Figure that for the highest concentrations of free morphine, the signal reduction (after magnetic washing W) is low, while for a low concentration of free morphine the signal reduction is high (a high concentration of MPs on the surface leading to a clear reduction in signal after magnetic washing W).

Figure 10:
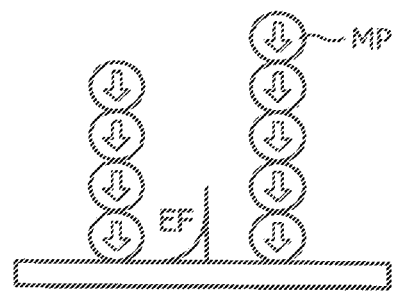
FIG. 10 illustrates the formation of pillars of magnetic beads in a magnetic field.

The signal reduction during actuation and magnetic relaxation as found in these experiments, together with information already collected from microscopic investigations proposes the following interpretation of the results: Upon magnetic actuation, MPs are concentrated to the surface, without showing an increase in binding to the surface (no signal decrease). Upon removing of the magnetic field, the signal drops indicating MPs binding to the surface. Application of a magnetic field then induces pillar formation: MPs become magnetized and those freely movable (a-specifically bound MPs and MPs freely in solution) will bind to the specific bound MPs in the direction of the magnetic field lines, which are perpendicular to the binding surface. This state is illustrated in FIG. 10, which also indicates the evanescent field EF. Since the evanescence detection system will only detect MPs at the surface, pillar formation during magnetic actuation will result in a reduction in signal change. Upon removal of the magnetic field, the MPs will lose their magnetic property, and fall to the surface again where binding can take place.

Figure 11:
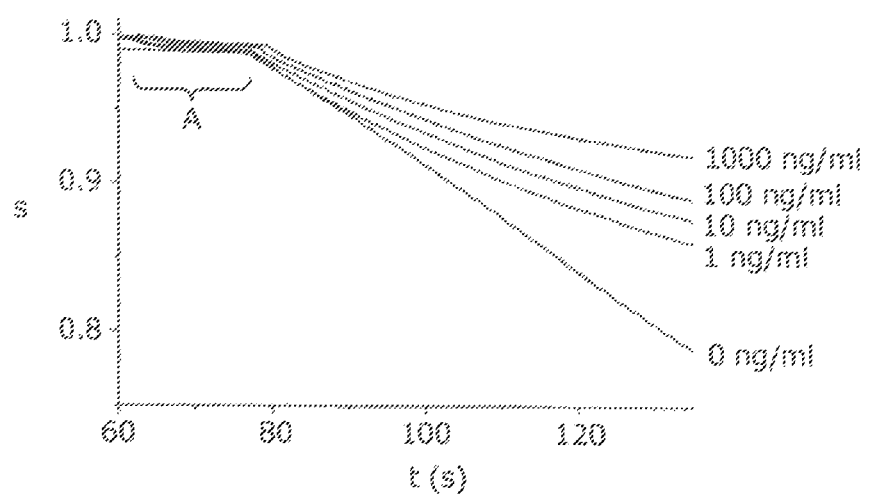
FIG. 11 is a diagram showing a normalized measurement signal s over time t for solutions with different concentrations of morphine labeled with magnetic particles when only one step of magnetic attraction is applied.

To obtain a fast assay, the actuation scheme can be optimized using the above results. FIG. 11 shows a dose-response curve on polystyrene wells coated with 10 pg/ml BSA-morphine. MPs functionalized with anti-morphine antibodies premixed with a defined amount of free morphine solved in PBS+10 mg/ml BSA+0.65% Tween-20 were inserted into the wells (1:20 dilution of MPs, total amount of solution was 40 µl, final morphine concentrations between 1 and 1000 ng/ml). MPs were actuated at A using a permanent magnet below the well for 15 seconds, to up-concentrate the MPs near the surface. Next, the MPs were allowed to bind to the surface for 60 seconds. The data show that already after 20 seconds the binding rate of magnetic particles to the surface is a direct measure for the concentration of free morphine in solution. This means that the measurement procedure can be simplified and more rapid, since no washing step is needed. For this to occur rapidly, the magnetic upconcentration step A is necessary.

Figure 12:
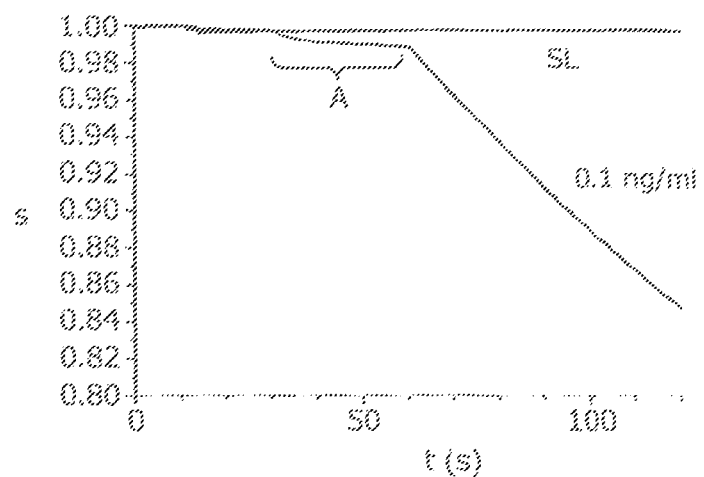
FIG. 12 is a diagram showing a normalized measurement signal s over time t for solutions containing saliva and morphine labeled with magnetic particles.

Next, the background signal from saliva was tested. Filtered saliva was introduced in a well and the signal was followed for 120 seconds. The background is negligible as can be seen in FIG. 12. As a comparison, the signal of MPs in PBS+10 mg/ml BSA+0.65% Tween20 mixed with 0.1 ng/ml morphine is included as well. At t=13 s, both the saliva (SL) and the morphine solution+MPs were injected. It can be seen that the background signal from the saliva is <1% and can be neglected.

Experimental Results B

Figure 13:
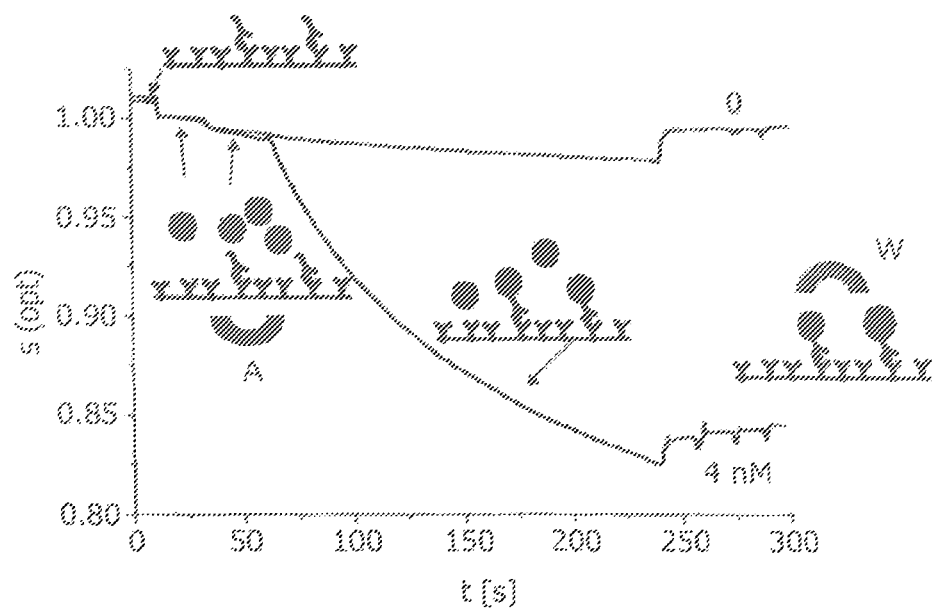
FIG. 13 is a diagram showing a normalized measurement signal s over time t for a two-step PTH assay in comparison to a solution containing no PTH.

To verify the sensitivity of the detection method a two-step PTH (PTH=parathyroid hormone) assay was carried out in the described well-plates on an optical substrate. In FIG. 13 the signal transients s (arbitrary units) are plotted as function of time t for both a blanc (0 nM, upper curve) and a relatively high (4 nM) concentration. A clear difference in the kinetic binding regime is observed and also a clear signal difference after washing W remains.

Figure 14:
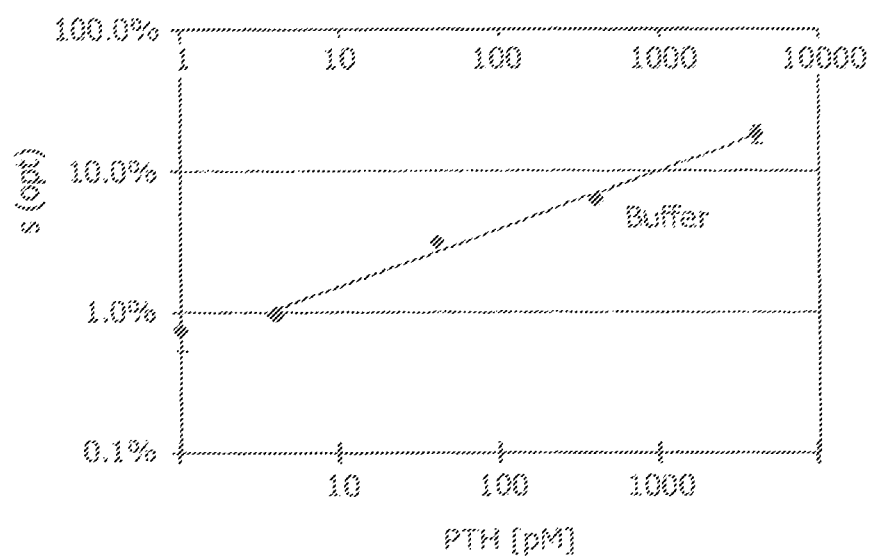
FIG. 14 shows a dose-response curve for PTH in buffer for optical detection.

In order to compare magnetic read-out (via Giant Magneto-Resistance (GMR) sensors as they are for example described in the WO 2005/010543 A1 or WO 2005/010542 A2) with optical read-out (via the principle of frustrated total internal reflection explained above), the PTH dose response curve is plotted in FIG. 14.

Figure 15:
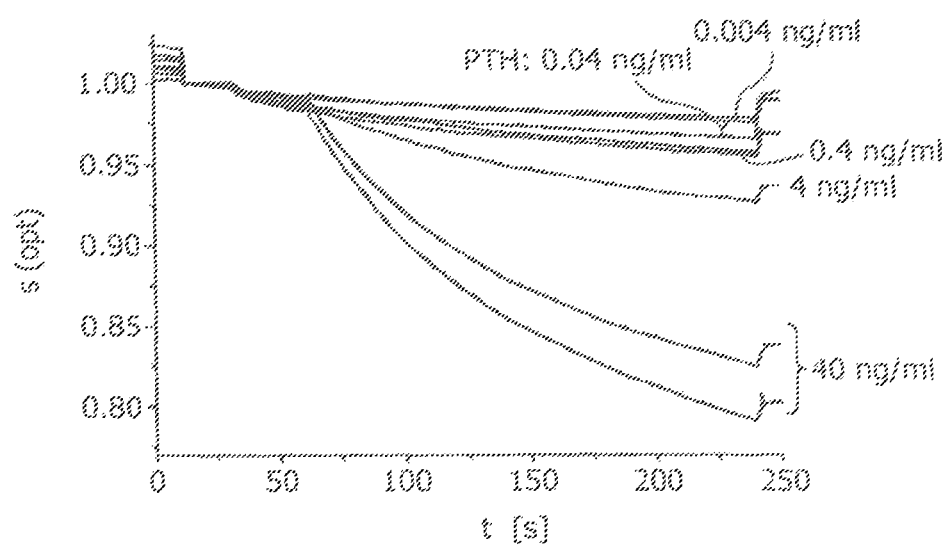
FIG. 15 is a diagram like that of FIG. 13 for different concentrations of PTH.

The corresponding transient curves for the optically detected PTH assay are given in FIG. 15. The dose-response curve in FIG. 14 is measured in a buffer matrix. The curve shows the optical signal s as percentage of the signal caused by reflection from an empty substrate. It is interesting to note that the curve is linear on a log-log scale (similar to the magnetically detected curve). Furthermore, detection limits can be calculated according to 'blanc+2*standard deviation of the blanc' (wherein "blanc" indicates the signal level when testing a sample with zero target concentration).

For the magnetic read-out this value is equal to 3 pM. For the optical experiment, which was done with a very basic experimental set-up, this value was equal to 13 pM. It can be concluded that both detection techniques seem to have the same sensitivity.

Figure 16:
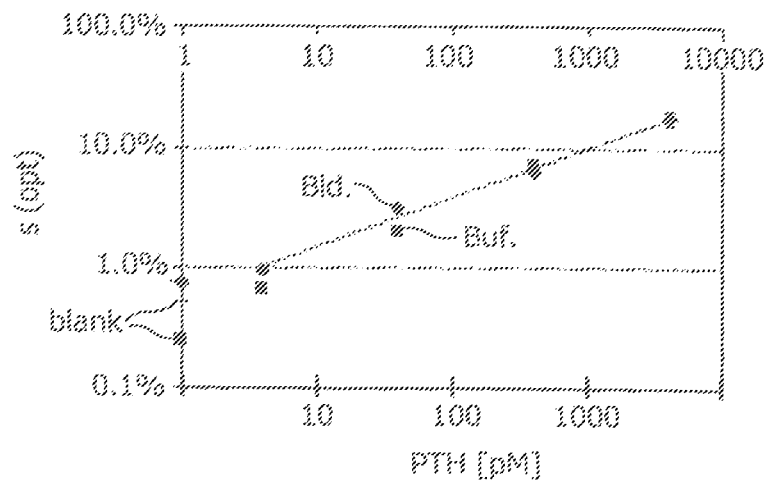
FIG. 16 shows a dose-response curve for PTH in buffer and in blood for optical detection.

Next it is very important to verify the background signal for the optical detection method when measuring in complex matrices. For this reason the same PTH assay was carried out in a blood matrix. From the results shown in FIG. 16 (Bld.=blood, Buf.=buffer) it is clear that the resulting dose-response very well matches the curve that was measured in buffer. Also the blank signal is very low. This nice property is attributed to the fact that the total internal reflection is caused by the refractive index difference between the optical substrate material and the matrix. The matrix can consist of different components such as plasma, (red blood) cells, etc. However, all these components have a significantly lower refractive index than the substrate material. Therefore, total internal reflection is not influenced by the matrix. Only when beads are bound (e.g. high-index polystyrene with magnetic grains) the total internal reflection is frustrated and a drop in reflected intensity can be measured.

Experimental Results C

Figure 17:
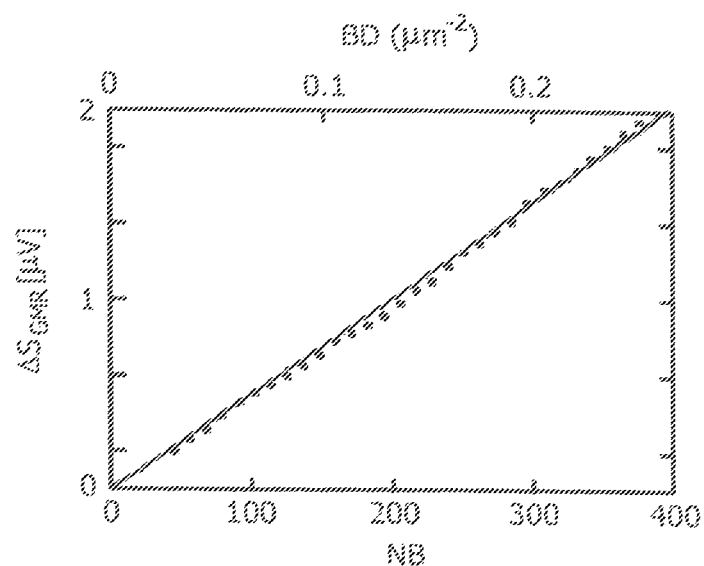
FIG. 17 shows a bead-response curve for detection with a GMR sensor.

An important proof for the proposed technology is the so-called bead-response curve. It gives an indication of the signal change per bead attached to the sensor surface. Ideally, detection of a single bead is possible (in presence of noise, disturbances). In this situation further improving the detection technology is not needed anymore. The biological detection limit can then only be improved by methods such as upconcentration of beads (in a catch-assay), etc. FIG. 17 shows the bead-response curve in case of detection with a GMR-type of sensor and 300 nm beads (Δs=signal change; BD=bead density; NB=number of beads). For these beads the detection limit was 3 beads on 40 μm² for a sampling frequency of 1 Hz.

Figure 18:
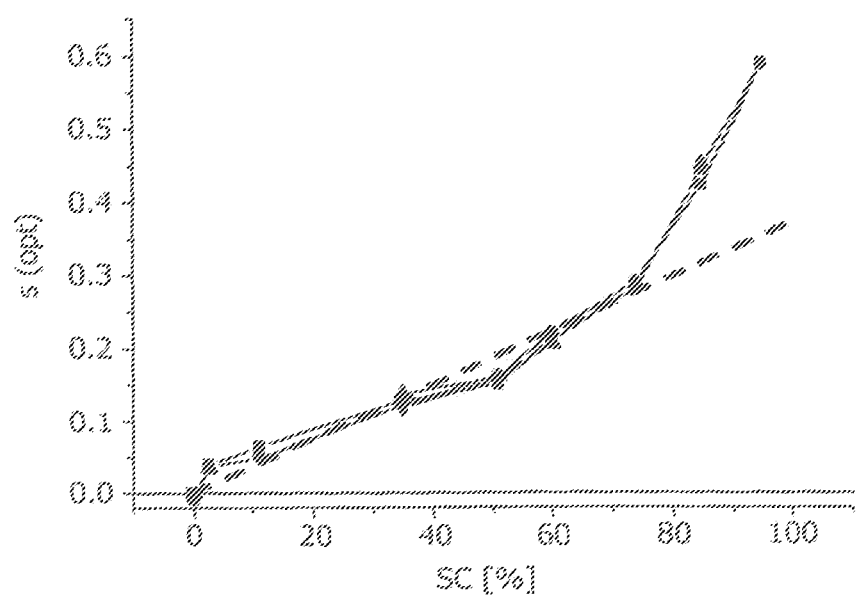
FIG. 18 shows a bead-response curve for optical detection.

In order to estimate the bead-response for optical detection, a number of samples (glass-slides) were prepared with various bead concentrations. The resulting surface coverage was determined using an optical microscope, followed by a measurement of the optical signal (change) s compared to a clean reference sample without beads. The experimental data as obtained with a simple set-up are plotted in FIG. 18. In this set-up, the noise level corresponds to a signal change at a surface coverage SC of 0.01%. These data show that the sensitivity of this technique is at least similar to state-of-the-art results using GMR sensors at the same bead concentrations.

In summary, the invention relates to a microelectronic sensor device for the detection of target components that comprise label particles, for example magnetic particles 1. The sensor device comprises a carrier 11 with a binding surface 12 at which target components can collect and optionally bind to specific capture elements. An input light beam L1 is transmitted into the carrier and totally internally reflected at the binding surface 12. The amount of light in the output light beam L2 is then detected by a light detector 31. Evanescent light generated during the total internal reflection interacts with the label particles 1 bound to target particles at the binding surface 12 leading to absorption and/or scattering and will therefore be missing in the output light beam L2. This can be used to determine the amount of target components at the binding surface 12 from the amount of light in the output light beam L2, L2a, L2b. A magnetic field generator 41 is optionally used to generate a magnetic field B at the binding surface 12 by which the magnetic label particles 1 can be manipulated, for example attracted or repelled.

The label particles 1 are for instance magnetic beads, which means magnetic particles MP, in an example paramagnetic, ferromagnetic, or super-paramagnetic particles or beads. These label particles 1 are subject to reflection of the light beam L1 impinging at the binding surface 12 of the carrier. The more label particles 1 are bound to the binding surface 12 the more the light beam L1 will not be totally internal reflected at the binding surface 12 but an evanescent wave will be generated. The light beam L2 reflected by the binding surface 12 is so called frustrated by the effect of scattering of the incoming light beam L1 by the label particles 1. The more label particles 1 bound to the binding surface the more the reflected light beam L2 is frustrated. The light detector 31, 131 measures the light beam L2 coming from the binding surface 12 and uses the reflected light beam L2 for measuring the amount of label particles 1 bound at the binding surface 12. The more label particles 1 bound to the binding surface 12 the more scattering of the light beam L1 due to the label particles 1 takes place with the generation of the evanescent wave. The label particles 1 enabling the effect described have for instance the following features. Magnetic beads of a width of roughly 300 nm of uniform superparamagnetic particles containing a polymer core shell structure. These label particles 1 or magnetic beads show a scatter of light beam L1 which is sufficient for detection of the reflected light beam L2 to determine the label particles 1. Label particles 1 of similar materials and widths are also feasible, for instance label particles 1 of a width of 200 nm. Nevertheless, the scatter of light from only the target components to which the label particles 1 bind is found not to be suitable for detection. This means the direct measurement of target components by frustrated internal reflection to measure the amount of these target components is not possible. The detection and subsequent calculation of the amount of target particles 1 is made possible by the scattering of light at the label particles 1. Herewith, no detection of fluorescence of fluorescent material is needed, as used in state of the art with other optical detection systems. Further in this context it is to be stressed that detection of fluorescence light emitted by the target components is an additional feature which is combinable with the described method and sensor device.

While the invention was described above with reference to particular embodiments, various modifications and extensions are possible, for example:

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio)chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink jetprinting on the optical substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A method for detection of target components comprising label particles, comprising:
   a) collecting the target components comprising label particles at a binding surface of a carrier, said label particles including light scattering and/or light absorbing particles;
   b) directing an input light beam into the carrier such that it is totally internally reflected in an investigation region at the binding surface, wherein at least a portion of the input light beam that is totally internally reflected leaves the binding surface as an output light beam;
   c) measuring an amount of light in the output light beam; and
   d) determining an amount of light of the input light beam that is missing in the output light beam due to scattering and/or absorbing of the input light beam by the label particles based on the measured amount of light in the output light beam to indicate a presence and/or an amount of the target components at the binding surface.

2. The method according to claim 1, wherein the label particles are manipulated by a magnetic or electrical field that attracts or repels the label particles from the investigation region.

3. The method according to claim 1, wherein determining the amount of light of the input light beam that is missing in the output light beam due to scattering and/or absorbing of the input light beam by the label particles includes steps of:
   measuring the amount of light in the input light beam;
   measuring the amount of light in the output light beam; and
   relating the measured amount of light in the input light beam to the measured amount of light in the output light beam.

4. The method according to claim 3, further comprising the step of indicating the presence and/or the amount of the target components at the binding surface based on the amount of light of the input light beam that is missing in the output light beam due to scattering and absorbing of the input light beam by the label particles.

* * * * *